United States Patent
Massarwa et al.

(10) Patent No.: US 12,156,737 B2
(45) Date of Patent: Dec. 3, 2024

(54) POINT-LIST LINKING TO THREE-DIMENSIONAL ANATOMY

(71) Applicant: Biosense Webster (Israel) Ltd., Yokneam (IL)

(72) Inventors: Fady Massarwa, Baka Al Gharbiyya (IL); Sigal Altman, Ramat Hashofet (IL); Assaf Cohen, Kiryat Bialik (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 398 days.

(21) Appl. No.: 17/502,578

(22) Filed: Oct. 15, 2021

(65) Prior Publication Data
US 2023/0119769 A1   Apr. 20, 2023

(51) Int. Cl.
*A61B 5/341*   (2021.01)
*A61B 5/283*   (2021.01)
(Continued)

(52) U.S. Cl.
CPC .............. *A61B 5/341* (2021.01); *A61B 5/283* (2021.01); *A61B 5/30* (2021.01); *A61B 5/367* (2021.01);
(Continued)

(58) Field of Classification Search
CPC ...... G06F 16/748; G06F 16/94; G06F 18/213; G06F 18/214; G06F 18/2431; G01T 1/161; G01C 11/00; G01C 15/002; G01B 11/002; G01B 11/24; C12Q 1/6806; C12Q 1/682; C12Q 2521/301; C12Q 2521/501; C12Q 2523/101; C12Q 2565/133;
(Continued)

(56) References Cited

U.S. PATENT DOCUMENTS 7,841,986 B2 * 11/2010 He ..................... A61B 5/0044
                                                            600/509
2003/0194057 A1 * 10/2003 Dewaele .................. G06T 7/60
                                                            378/210
(Continued)

FOREIGN PATENT DOCUMENTS

EP   3254618 A1   12/2017
EP   3461402 A1   4/2019
EP   3878354 A1   9/2021

OTHER PUBLICATIONS

European Search report for corresponding EPA No. 22201515.8 dated Feb. 28, 2023.

*Primary Examiner* — Negussie Worku
(74) *Attorney, Agent, or Firm* — Volpe Koenig

(57) ABSTRACT

Systems and methods are disclosed for linking a point-list to a three-dimensional anatomy of the heart. Techniques disclosed include recording a point-list, where each entry in the point-list comprises data elements, and is associated with a location in the heart and a measurement. The associated measurement is acquired by an electrode of a catheter that is placed at the associated location in the heart. Techniques disclosed further include selecting one or more anchor points associated with a region of interest in the heart, then, for each entry in the recorded point-list, computing a data element of distance between the entry's associated location in the heart and the selected one or more anchor points, and manipulating entries in the point-list based on their respective data elements.

28 Claims, 7 Drawing Sheets

(51) Int. Cl.
*A61B 5/30* (2021.01)
*A61B 5/367* (2021.01)
*G06T 7/00* (2017.01)
*G06T 7/70* (2017.01)
*G06T 11/00* (2006.01)
*G16H 10/60* (2018.01)
*G16H 30/40* (2018.01)
*G16H 50/20* (2018.01)
*G16H 50/70* (2018.01)

(52) U.S. Cl.
CPC .............. *G06T 7/0012* (2013.01); *G06T 7/70* (2017.01); *G06T 11/00* (2013.01); *G16H 10/60* (2018.01); *G16H 30/40* (2018.01); *G16H 50/20* (2018.01); *G16H 50/70* (2018.01); *G06T 2207/30048* (2013.01)

(58) Field of Classification Search
CPC .......... C12Q 2565/501; Y10S 128/922; G06V 10/25; G06V 10/44; G06V 10/454; G06V 10/46; G06V 10/7715; G06V 10/82; G06V 10/95; G06V 20/20; G06V 20/52; G06V 2201/03; G06V 30/14; G06V 30/147; G01R 33/563; G01R 33/56333; A61F 2002/4633; G16H 10/60; G16H 30/40; G16H 50/20; G16H 50/70; A61B 5/055; A61B 34/20; A61B 6/508; A61B 17/1703; A61B 17/3462; A61B 2017/00477; A61B 2017/3407; A61B 2017/3492; A61B 2034/2046; A61B 2034/2074; A61B 5/283; A61B 5/30; A61B 5/341; A61B 5/343; A61B 5/367; A61B 5/743; A61B 90/11; A61B 5/4519; A61B 5/7257; A61B 6/5205; A61B 2034/2048; A61B 2034/2051; A61B 2090/367; A61B 2090/376; A61B 6/032; A61B 6/12; A61B 6/4441; A61B 6/487; A61B 6/50; A61B 6/504; A61B 6/5223; A61B 6/5235; A61B 6/547; G06T 7/0012; G06T 2207/30008; G06T 7/33; G06T 7/62; G06T 11/00; G06T 2207/30048; G06T 7/70; G06T 2207/10081; G06T 2207/30061; G06T 2207/30101; G06T 3/00; G06T 7/60; G06T 7/66; G06T 7/75; G06T 19/006; G06T 2207/10088; G06T 2207/10116; G06T 2207/10121; G06T 2207/20016; G06T 2207/20081; G06T 2207/20084; G06T 2207/30056; G06T 2207/30096; G06T 2207/30172; G06T 3/4046; G06T 5/70; G06T 7/10; G06T 7/20
USPC ......................................... 358/1.15; 382/128
See application file for complete search history.

(56) References Cited

U.S. PATENT DOCUMENTS

| | | | |
|---|---|---|---|
| 2006/0270976 A1* | 11/2006 | Savage | A61M 25/0147 604/95.04 |
| 2008/0058794 A1 | 3/2008 | MacAdam et al. | |
| 2010/0268059 A1* | 10/2010 | Ryu | A61N 1/3627 600/407 |
| 2010/0286551 A1* | 11/2010 | Harlev | A61B 5/0538 600/547 |
| 2014/0276783 A1* | 9/2014 | Srivastava | A61B 18/02 606/41 |
| 2019/0164633 A1 | 5/2019 | Ingel | |
| 2020/0022808 A1* | 1/2020 | Matheny | A61F 2/2412 |
| 2022/0175323 A1* | 6/2022 | Montag | A61B 5/287 |
| 2022/0233818 A1* | 7/2022 | Osadchy | A61B 5/283 |
| 2022/0238218 A1* | 7/2022 | Eliyahu | A61B 5/7267 |
| 2022/0335725 A1* | 10/2022 | Taheri | G06V 20/52 |
| 2024/0116520 A1* | 4/2024 | Meng | B60W 50/00 |

* cited by examiner

300

400

500

US 12,156,737 B2

POINT-LIST LINKING TO THREE-DIMENSIONAL ANATOMY

BACKGROUND

Cardiac arrhythmias such as atrial fibrillation, ventricular fibrillation, ventricular tachycardia, or atrial flutter may cause morbidity and death. Treatments for cardiac arrhythmia often require obtaining a detailed cardiac electro-anatomical mapping of the heart. Such mapping, performed during electrophysiological procedures, assists in localization and characterization of the cardiac arrhythmia in the heart and informs physician decisions on a course of treatment.

Electro-anatomical mapping of the heart provides a three-dimensional (3D) representation of the anatomy of the heart (i.e., an anatomical map) overlaid by electrical properties of heart tissue (i.e., an electrical map). A visualization system, such the CARTO® 3 3D mapping system of Biosense Webster, can be used by a physician to reconstruct the anatomical and electrical maps of the heart. Such reconstruction may involve acquisition of electrical signals measured by electrodes of a catheter placed at various locations on the endocardial wall. The system may then maintain a point-list that records, for each point (or entry in the list), the electrode's location at which a corresponding electrical signal has been measured and associated data. Based on the data recorded in the point-list, the system may generate an electro-anatomical map.

During an electrophysiological procedure, to facilitate the reconstruction of a detailed electro-anatomical map, a physician may have to acquire thousands of measurements, typically using a multielectrode catheter, from regions of the heart that may be exhibiting abnormal electrical activity. Accordingly, the system may generate a point-list that may include thousands of entries. The point-list may be presented to the physician in a scrollable window together with a presentation of the electro-anatomical map. The physician may then be required to analyze and compare data of entries in the point-list that correspond to a region of interest in the electro-anatomical map. However, since the point-list is not linked to the anatomy, entries that correspond to tissue locations in close proximity to each other may be thousands of entries apart in the point-list. As only a small number of entries can be concurrently viewed in a scrollable window, visually comparing data across entries that correspond to neighboring tissue locations is cumbersome and not practical. Techniques are needed to allow efficient navigation through a point-list that will reduce the electrophysiological procedure time and improve the accuracy of the arrhythmia condition diagnosis and the decision on a course of treatment.

SUMMARY

Aspects disclosed in the present application describe methods for linking a point-list to a three-dimensional anatomy of the heart. The methods comprise recording a point-list. Each entry in the point-list comprises data elements, and is associated with a location in the heart and a measurement, wherein the associated measurement is acquired by an electrode, of a catheter, placed at the associated location in the heart. The methods further comprise selecting one or more anchor points associated with a region of interest in the heart; computing, for each entry in the point-list, a data element of distance between the location associated with the entry in the heart and the selected one or more anchor points; and manipulating entries in the point-list based on their respective data elements.

Aspects disclosed in the present application also describe systems for linking a point-list to a three-dimensional anatomy of the heart. The systems comprise at least one processor and memory storing instructions. The instructions, when executed by the at least one processor, cause the systems to record a point-list. Each entry in the point-list comprises data elements, and is associated with a location in the heart and a measurement, wherein the associated measurement is acquired by an electrode, of a catheter, placed at the associated location in the heart. The instructions further cause the systems to select one or more anchor points associated with a region of interest in the heart; compute, for each entry in the point-list, a data element of distance between the location associated with the entry in the heart and the selected one or more anchor points; and manipulate entries in the point-list based on their respective data elements.

Further, aspects disclosed herein describe a non-transitory computer-readable medium that comprises instructions executable by at least one processor to perform methods for linking a point-list to a three-dimensional anatomy of the heart. The methods comprise recording a point-list. Each entry in the point-list comprises data elements, and is associated with a location in the heart and a measurement, wherein the associated measurement is acquired by an electrode, of a catheter, placed at the associated location in the heart. The methods further comprise selecting one or more anchor points associated with a region of interest in the heart; computing, for each entry in the point-list, a data element of distance between the location associated with the entry in the heart and the selected one or more anchor points; and manipulating entries in the point-list based on their respective data elements.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
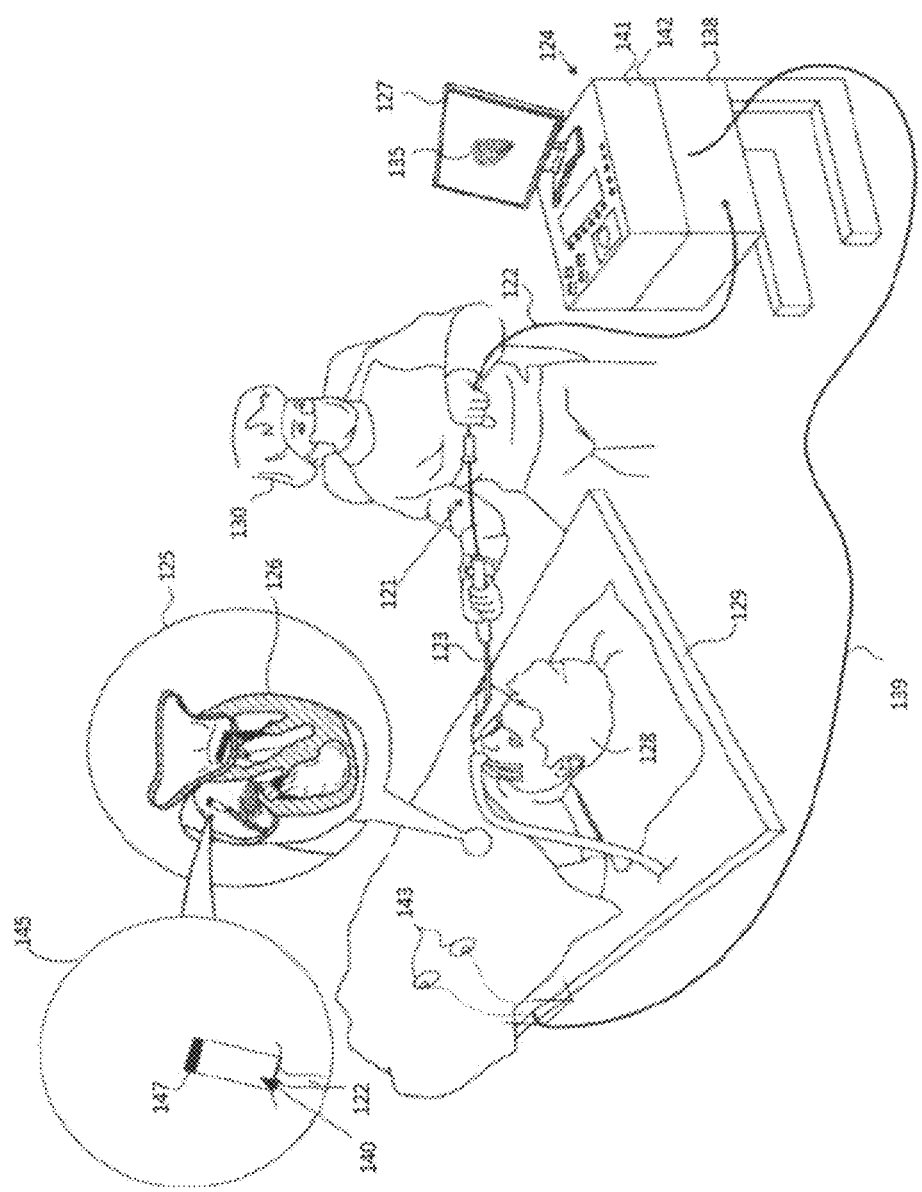
FIG. 1 is a diagram of an example cardiac ablation system, based on which one or more features of the disclosure may be implemented.

In patients with normal sinus rhythm, the heart, containing atrial and ventricular excitatory conduction tissue, is electrically excited to beat in a synchronous and patterned fashion. In patients with cardiac arrhythmias, abnormal regions of cardiac tissues do not follow the synchronous beating cycle associated with normally conductive tissues. Instead, the abnormal regions of cardiac tissue aberrantly conduct to adjacent tissue, thereby disrupting the cardiac cycle into an asynchronous cardiac rhythm. Such an abnormal conduction may occur at various regions of the heart, for example, in the region of the sinoatrial (SA) node, along the conduction pathways of the atrioventricular (AV) node and the Bundle of His, or in the cardiac muscle tissue that forms the walls of the ventricular and atrial cardiac chambers.

Cardiac arrhythmias may be of a multiwavelet reentrant type, characterized by multiple asynchronous loops of electrical pulses that are scattered about the heart chamber and are often self-propagating. Alternatively, or in addition to the multiwavelet reentrant type, cardiac arrhythmias may also have a focal origin, such as when an isolated region of heart tissue fires autonomously in a rapid and repetitive fashion. Abnormal electrical activity that originates in the ventricles, for example, can cause a ventricular tachycardia (a fast heart rhythm), a potentially life-threatening arrhythmia that may lead to ventricular fibrillation and sudden death. Another type of arrhythmia, atrial fibrillation, may occur when the normal electrical pulses generated by the sinoatrial node are overwhelmed by disorganized electrical pulses that originate in the atria and pulmonary veins and cause irregular pulses to be conducted to the ventricles. Cardiac arrhythmias can be treated by medication or synchronized electrical cardioversion that either slow the heart rate or revert the heart rhythm back to normal. Alternatively, cardiac arrhythmias can be treated by ablation of the cardiac tissue.

A catheter ablation-based treatment involves selectively ablating cardiac tissue by the application of energy. The ablation process damages the unwanted electrical pathways through the formation of non-conductive lesions. Energy delivery modalities use microwave, laser, and, more commonly, radiofrequency energies to create conduction blocks along the cardiac tissue walls. Typically, an ablation procedure begins with an electro-anatomical mapping phase, during which the sources of the abnormal electrical activity are investigated and discovered. The mapping phase is followed by an ablation phase, in which tissue at the discovered sources are ablated. Then, a validation phase is carried out, in which the effect of the ablation is evaluated. Thus, the mapping phase is critical as its accuracy enables effective termination of the abnormal electrical activity, that is, the arrhythmia condition. The mapping of the heart includes reconstruction of the 3D anatomy of the heart as well as overlaying electrical properties onto that reconstructed anatomy. The electrical properties may be derived from electrical signals measured by electrodes of a catheter that is placed at various locations in the heart. According to aspects described herein, the electro-anatomical map may be utilized by the physician to determine endocardial target areas at which ablation is to be performed.

Cardiac ablation and other cardiac electrophysiological procedures have become increasingly complex as clinicians treat challenging conditions such as atrial fibrillation and ventricular tachycardia. The treatment of complex arrhythmias can now rely on systems, such as the CARTO® 3 3D mapping system. The CARTO® 3 system can provide 3D visualization of the heart anatomy overlaid with maps that visualize electrical properties of the heart, derived from acquired measurements of electrical signals. In addition to the electro-anatomical map, the CARTO® 3 system can present to the physician a point-list that records data associated with the acquired measurements of electrical signals. Aspects disclosed herein describe systems and methods with which a physician can efficiently navigate through a point-list and explore data entries that correspond to an anatomical region of interest.

FIG. 1 is a diagram of an example cardiac ablation system 100, in which one or more features of the disclosure may be implemented. The system 100 may include a console 124, a display 127, and a catheter 140, operated by a user (e.g., a physician or a medical professional) 130. The system 100 may be configured to obtain anatomical and electrical measurements, taken from an organ of a patient 128 such as the heart 126, to visualize the obtained anatomical and electrical measurements, and to perform a cardiac ablation procedure. Inset 145 shows the catheter 140 in an enlarged view and inset 125 shows the catheter 140 inside a cardiac chamber of the heart 120. An example of system 100 is the CARTO® 3 3D mapping system of Biosense Webster.

The catheter 140 shown in FIG. 1 is representative herein of one or more catheters that may be employable by the cardiac ablation system 100, including an ablation catheter and a sensing catheter. An ablation catheter may be configured to damage (ablate) tissue areas of an intra-body organ. A sensing catheter, equipped with one or more electrodes, may be configured to obtain biometric data including electric signals. The system 100 may include one or more probes 121, having shafts 122 that may be navigated by a physician 130 into a body part, such as the heart 126, of a patient 128 lying on a table 129. The physician 130 may insert a shaft 122 through a sheath 123, while manipulating the distal end of the shafts 122 using a manipulator near the proximal end of the catheter 140 and/or while deflecting from the sheath 123. As shown 145, the catheter 140 may be fitted at the distal end of the shaft 122. The catheter 140 may be inserted through the sheath 123 in a collapsed state and may then be expanded within the heart 126.

In an aspect, electrical properties of the heart (e.g., biometric data derived from electrical signals acquired by catheters' electrodes) may represent information associated with a local arrival time (LAT), an electrical activity, a topology, a unipolar or a bipolar voltage, a dominant frequency, or an impedance, for example. A LAT may represent a time at which an electrical activity has been measured at a certain location. The LAT may be calculated based on a normalized initial starting point that may be derived from a reference catheter. An electrical activity may be any applicable electrical signal that may be measured based on one or more thresholds. The electrical activity may be augmented (e.g., using filters to improve the signal to noise ratios). A topology may represent the physical structure of a body part or a portion of a body part or may correspond to changes in the physical structure between different portions of the body part or between different body parts. A dominant frequency may represent a frequency, or a range of frequencies, that is prevalent in a portion of a body part and may be different in different portions of the same body part. For example, the dominant frequency of a pulmonary vein in the heart may be different from the dominant frequency of the right atrium of the same heart. An impedance may represent resistance at a given area of a body part.

The console 124 of the system 100 may include a processing unit 141, memory 142, and communications interface circuitry 138. The processing unit 141 may be a computer equipped with a multi-core processor and may comprise a front end and control components. The memory 142 may comprise volatile and/or non-volatile memory. The communications interface circuitry 138 may be used for transmitting and receiving signals to and from the catheter 140. The console 124 may be configured to receive biometric data, and then, to process, to visualize, and to store the biometric data for later processing, or to transmit the data to another system via a network. In an aspect, the processing unit 141 may be external to the console 124 and may be located, for example, in the catheter 140, in an external device, in a mobile device, in a cloud-based device, or may be a standalone processor. The processing unit 141 may execute software modules programmed to carry out the functions of aspects described herein. The software modules may be downloaded to the processing unit 141 over a network or from non-transitory tangible media, such as magnetic, optical, or electronic memory, external or local to the console 124.

The system 100 may be modified to implement aspects disclosed herein. Aspects disclosed herein may be similarly applied using other system components and settings. Additionally, the system 100 may include additional components, such as elements for sensing electrical activity, wired or wireless connectors, processing units, or display devices. The console 124 may include real-time noise reduction circuitry typically configured as a field programmable gate array (FPGA), followed by an analog-to-digital (A/D) ECG (electrocardiograph) or EMG (electromyogram) signal conversion integrated circuit. The output of the A/D ECG or EMG circuit may be processed to perform methods disclosed herein.

The console 124 may be connected, by a cable 139, to body surface electrodes 143, which may include adhesive skin patches that are affixed to the patient 128. The processing unit 141, in conjunction with a tracking module, may determine position coordinates of the catheter 140 inside a body part (e.g., the heart 126) of the patient 128. The position coordinates may be based on impedances or electromagnetic fields measured between the body surface electrodes 143 and electrodes (or other electromagnetic components) of the catheter 140. Additionally, or alternatively, the position coordinates may be based on impedances or electromagnetic fields measured between location pads attached to the surface of the bed 129 and electrodes (or other electromagnetic components) of the catheter 140.

During a procedure, the processing unit 141 may facilitate the rendering 135 of a body part 126 on the display 127 to be viewed by the physician 130 and may store data representing the body part in the memory 142. In an aspect, the physician 130 may be able to rotate and move the rendered body part 135 (e.g., change the point of view of the rendered body part) using one or more input devices, such as a touchscreen, a touch pad, a mouse, a keyboard or a gesture recognition apparatus. For example, the position of the catheter 140 may be change to collect measurements based on which the rendering 135 of a body part 126 is updated. Additionally, a representation of the catheter may be rendered in relation to the rendering of the body part, to allow the physician 130 to better navigate the catheter within the body part. In an aspect, the display 127 may be located at a remote location such as a separate hospital or in separate healthcare provider networks.

Figure 2:
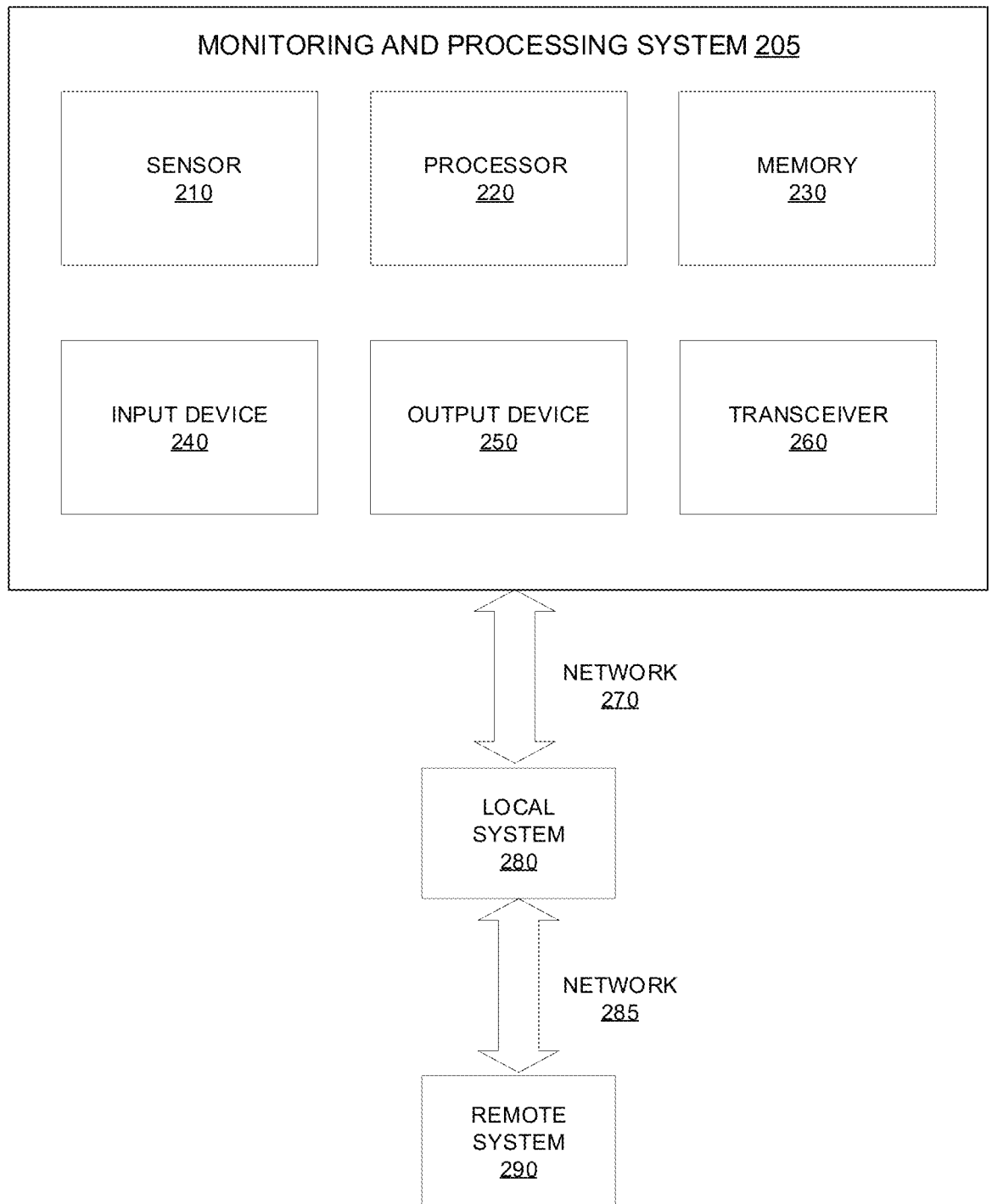
FIG. 2 is a block diagram of an example system, deployable by the example cardiac ablation system of FIG. 1, based on which one or more features of the disclosure may be implemented.

FIG. 2 is a block diagram of an example system 200, deployable by the example cardiac ablation system of FIG. 1, based on which one or more features of the disclosure may be implemented. The system 200 may include a monitoring and processing system 205, a local system 280, and a remote system 290. The monitoring and processing system 205 may include a sensor 210, a processor 220, memory 230, an input device 240, an output device 250, and a transceiver 260, e.g., a transmitter-receiver in communication with a network 270. The system 205 may continually or periodically monitor, store, process, and communicate, via the network 270, various patient biometric data. Patient biometric data may include electrical signals (e.g., ECG signals), anatomical images, blood pressure data, blood glucose data, and temperature data, for example. The patient biometric data may be monitored (processed, visualized, communicated) to facilitate treatment of various diseases, such as cardiovascular diseases (e.g., arrhythmias, cardiomyopathy, and coronary artery disease) and autoimmune diseases (e.g., type I and type II diabetes).

In an aspect, the monitoring and processing system 205 may represent the console 124 of the system 100 shown in FIG. 1. In another aspect, the monitoring and processing system 205 may be internal to the patient's body—e.g., the system 205 may be subcutaneously implantable, inserted orally or surgically, via a vein or an artery, via an endoscopic or a laparoscopic procedure. In yet another aspect, the system 205 may be externally attached to the patient's skin. Alternatively, the system 205 may include components that are internal to the patient's body and components that are external to the patient's body.

The monitoring and processing system 205, may represent a plurality of monitoring and processing systems 205 that may process biometric data of a patient in parallel, in communication with each other and/or in communication with a server via a network. One or more systems 205 may acquire or receive all or part of a patient's biometric data (e.g., electrical signals, anatomical images, blood pressure, temperature, blood glucose level, or other biometric data). The one or more systems 205 may also acquire or receive additional information associated with the acquired or received patient's biometric data from one or more other systems 205. The additional information may be, for example, diagnosis information and/or information obtained from a device such as a wearable device. Each monitoring and processing system 205 may process data acquired by it and may process data received from another system 205.

The sensor 210 may represent one or more sensors that may be configured to sense biometric data from a patient. For example, the sensor 210 may be an electrode configured to acquire electrical signals (e.g., bioelectrical signals originating in the heart), a temperature sensor, a blood pressure sensor, a blood glucose sensor, a blood oxygen sensor, a pH sensor, an accelerometer, or a microphone. In an aspect, system 205 may comprise an ECG monitoring system that measures ECG signals originating in the heart. In such a case, the sensor 210 may include one or more electrodes that may be configured to acquire the ECG signals. The ECG signals may be used to diagnose and treat various cardiovascular diseases. In an aspect, the sensor 210 may include a catheter with one or more electrodes, a probe, a blood pressure cuff, a weight scale, a bracelet (e.g., a smart watch biometric tracker), a glucose monitor, a continuous positive airway pressure (CPAP) machine, or any other device that provides biometric data or other data concerning the patient's health.

The transceiver 260 may include a transmitter component and a receiver component. These transmitter component and receiver component may be integrated into a single device or separately implemented. The transceiver may provide connectivity between the system 205 and other systems or servers via a communication network 270. The network 270 may be a wired network, a wireless network or include a combination of wired and/or wireless networks. The network 270 may be a short-range network (e.g., a local area network (LAN) or a personal area network (PAN)). Information may be sent or may be received via the short-range network using various short-range communication protocols such as Bluetooth, Wi-Fi, Zigbee, Z-Wave, near field communications (NFC), ultra-band, or infrared (IR). The network 270 may also be a long-range network (e.g., wide area network (WAN), the internet, or a cellular network). Information may be sent or may be received via the long-range network using various long-range communication protocols such as TCP/IP, HTTP, 3G, 4G/LTE, or 5G/New Radio.

The processor 220 may be configured to process patient's biometric data, for example, obtained by the sensor 210, and store the biometric data and/or the processed biometric data in memory 230. The processor 220 may also be configured to communicate the biometric data across the network 270 via a transmitter of the transceiver 260. Biometric data from one or more other monitoring and processing systems 205 may be received by a receiver of the transceiver 260. The processor 220 may employ algorithms (e.g., artificial-intelligence-based algorithms such as machine learning algorithms), or, alternatively or in addition, algorithms may be employed by other processors (e.g., at the local system 280 or the remote system 290). In aspects, the processor 220 may include one or multiple CPUs, one or multiple GPUs, or one or multiple FPGAs. In these aspects, the algorithms may be executed on one or more of these processing units. Similarly, the processor 220 may include an ASIC dedicated to performing deep learning calculations (such as the Intel® Nervana™ Neural Network Processor) and machine learning algorithms may be executed on such dedicated ASIC. The processing unit that executes the algorithms may be located in the medical procedure room or in another location (e.g., another medical facility or a cloud).

The input device 240 of the monitoring and processing system 205 may be used as a user interface. The input device 240 may include, for example, a piezoelectric sensor or a capacitive sensor that is configured to receive user input, such as tapping or touching. Hence, the input device 240 may be configured to implement capacitive coupling in response to tapping or touching a surface of the system 205 by a user. Gesture recognition may be implemented by various capacitive coupling such as resistive capacitive, surface capacitive, projected capacitive, surface acoustic wave, piezoelectric, or infra-red touching. Capacitive sensors may be placed on the surface of the input device 240 so that the tapping or touching of the surface activates the system 205. The processor 220 may be configured to respond selectively to different tapping patterns of the capacitive sensor (e.g., a single tap or a double tap on the input device 240) such that different functions of the system 205 (e.g., acquisition, storing, or transmission of data) may be activated based on the detected pattern. In an aspect, audible feedback may be given to the user from the system 205, e.g., when a gesture is detected and recognized.

The local system 280, that may be in communication with the monitoring and processing system 205 via the network 270, may be configured to act as a gateway to the remote system 290 through another network 285 that may be accessible to the local system 280. The local system 280 may be, for example, a smart phone, smartwatch, tablet, or other portable smart device. Alternatively, the local system 280 may be a stationary or a standalone device. Patient biometric data may be communicated between the local system 280 and the monitoring and processing system 205. In an aspect, the local system 280 may also be configured to display the acquired patient biometric data and associated information.

The remote system 290 may be configured to receive at least part of the monitored patient biometric data and associated information via the network 285, which may be a long-range network. For example, if the local system 280 is a mobile phone, network 285 may be a wireless cellular network, and information may be communicated between the local system 280 and the remote system 290 via a wireless technology standard, such as any of the wireless technologies mentioned above. The remote system 290 may be configured to present received patient biometric data and the associated information to a healthcare professional (e.g., a physician), either visually on a display or aurally through a speaker.

Figure 3:
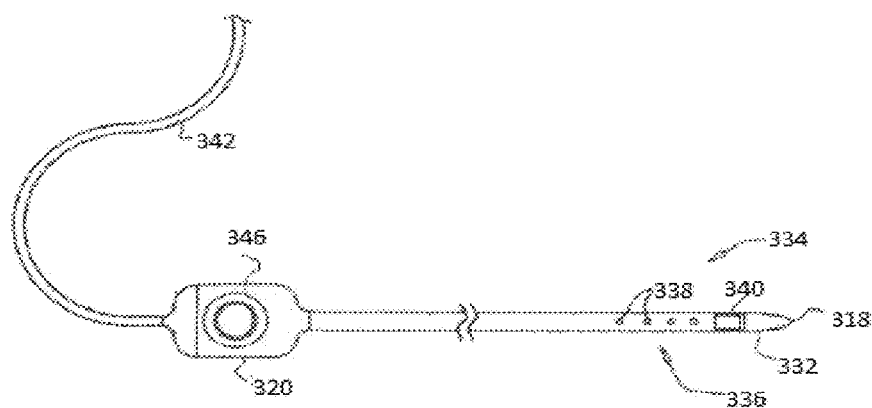
FIG. 3 illustrates an example catheter, based on which one or more features of the disclosure may be implemented.
Figure 4:
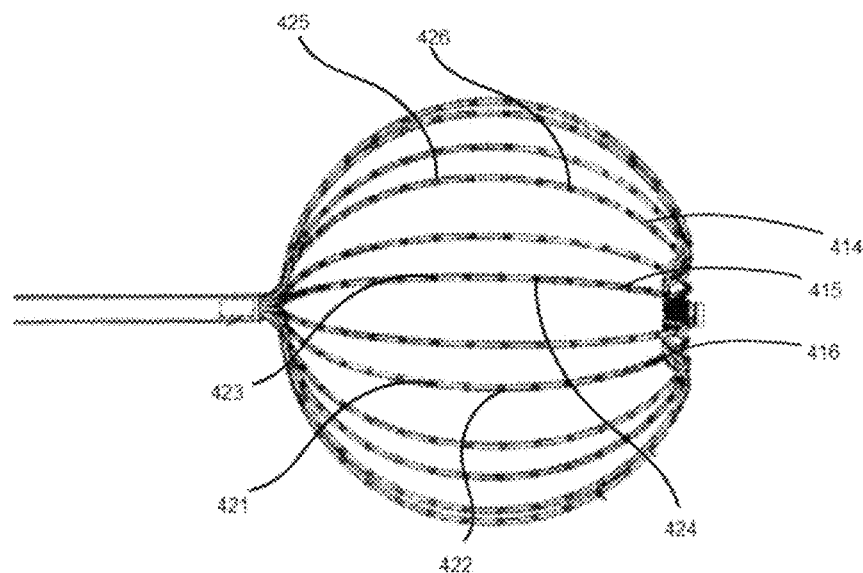
FIG. 4 illustrates an example balloon catheter, based on which one or more features of the disclosure may be implemented.
Figure 5:
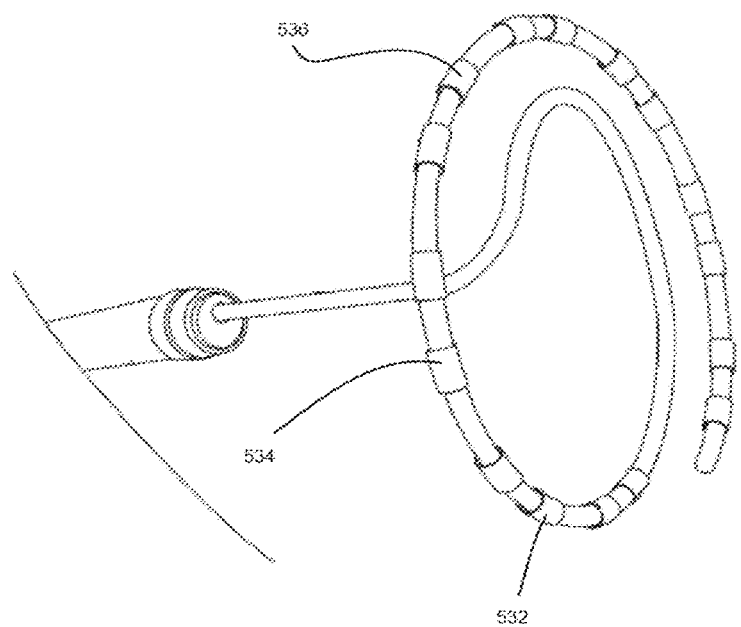
FIG. 5 illustrates an example loop catheter, based on which one or more features of the disclosure may be implemented.

FIGS. 3, 4, and 5 illustrate, respectively, example catheters 300, 400, 500. Electrodes or sensors, disposed on the distal portion of the catheters 300, 400, 500, may be used to measure electrical signals originating at the heart tissue that may be used for anatomical and electrical mapping. Other electrodes or sensors may be used to emit electrical signals into the heart tissue, for example, for therapeutic purposes (ablation) and/or catheter localization.

FIG. 3 illustrates a catheter 300 that include a contact electrode 332 and non-contact electrodes 338. The non-contact electrodes may measure far-field electrical signals in the heart chamber and may be arranged in an array 336 along the longitudinal axis of a distal portion 334 of the catheter 300. The distal portion 334 may further include a position sensor 340 (or multiple position sensors) that can generate or measure signals used to determine the sensor's 340 position and orientation. As there is a fixed spatial relation between the position sensor 340 and the distal tip 318 and other electrodes 332, 338, the positions of the distal tip 318 and the other electrodes 332, 338 can be resolved based on the determined position of the position sensors 340. The handle 320 of the catheter 300 may include controls 346 to steer or deflect the distal portion 334, or to orient it as desired.

For example, the position sensor 340 may be configured to sense an electrical field that may be produced by the system 100, 200 (for sensor localization purposes) and to transmit signals generated from the sensed field over a cable 342 running through the catheter 300 to the console 124 (that is, cable 122 shown in FIG. 1). In another alternative, the position sensor 340 may transmit the signals to the console 124 over a wireless link. Based on the signals sent by the position sensor 340, the processing unit 141, 220 may calculate the location and the orientation of the distal portion 334 of the catheter 300 as well as the location and the orientation of the distal tip 318 and the other electrodes 332, 338. The location and the orientation calculations may be carried out based on the signals sent by the position sensor 340 after those signals were amplified, filtered, digitized, or otherwise processed by the system 100, 200.

To acquire electrical activity at a point in the heart, a catheter 300 may be advanced into the heart and its distal tip 318 may be brought in contact with the endocardium at a certain tissue location to acquire data at that location. To construct an anatomical and electrical map of the heart, this data acquisition process has to be repeated for a large number of locations within a region of interest. Constructing a detailed map of a region of interest in the heart via such a point-by-point data accumulation process may take a long period of time. To address this shortcoming, multiple-electrode catheters have been developed to simultaneously measure electrical activity at multiple location points in the heart. Multielectrode catheters may be implemented using any applicable shape such as a balloon catheter (described in reference to FIG. 4) or a loop catheter (described in reference to FIG. 5).

FIG. 4 illustrates an example balloon catheter 400, based on which one or more features of the disclosure may be implemented. As shown in FIG. 4, a balloon catheter 400 may include multiple splines, such as splines 414, 415, 416. Multiple electrodes are disposed on each spline, such as electrodes 421-426, shown in FIG. 4. The balloon catheter 400 may be designed such that when deployed into a patient's body, its electrodes may be held in close contact against an endocardial surface. For example, a balloon catheter may be inserted into a lumen, such as a pulmonary vein. The balloon catheter may be inserted into the pulmonary vein in a deflated state such that the balloon catheter does not occupy its maximum volume while being inserted. The balloon catheter may then be expanded while inside the pulmonary vein such that the electrodes on the balloon catheter come into contact with an entire circular section of the pulmonary vein. Such contact with an entire circular section of the pulmonary vein, or any other lumen, may enable measurement of the electrical activity from multiple points on the tissue. That is, each an acquisition may result in as many signal measurements as the number of electrodes.

FIG. 5 illustrates an example loop catheter 500, based on which one or more features of the disclosure may be implemented. A loop catheter 500 (also referred to as a lasso catheter) may include multiple electrodes 532, 534, 536 that when brought in contact with the heart tissue (endocardial wall) may simultaneously acquire electrical signals measured at the locations of the electrodes. A loop catheter 500 may be fully or partially elastic such that it can twist, bend, and or otherwise change its shape based on a received signal and/or based on the application of an external force (e.g., when pushed against cardiac tissue).

Hence, a multielectrode catheter (such as a balloon catheter 400 or a loop catheter 500) may be advanced into a chamber of the heart to acquire electrical signals. Position sensors disposed on the multielectrode catheter (at a known spatial relation to the electrodes) may be used by the system 100, 200 to establish the locations in the heart of each of the electrodes. The electrical signals that are measured by each electrode may be recorded and may be presented to a physician on the display 127 by the system 100, 200. For example, the measured electrical signals may be presented as vertically aligned electrograms that are temporally correlated according to a reference signal. Typically, the reference signal is measured by a dedicated reference electrode that may be placed, for example, at the coronary sinus (CS). Thus, when using a multielectrode catheter that is equipped with many electrodes (each electrode being positioned on the endocardial surface) the physician may collect a set of measurement points as many as the number of electrodes.

Figure 6:
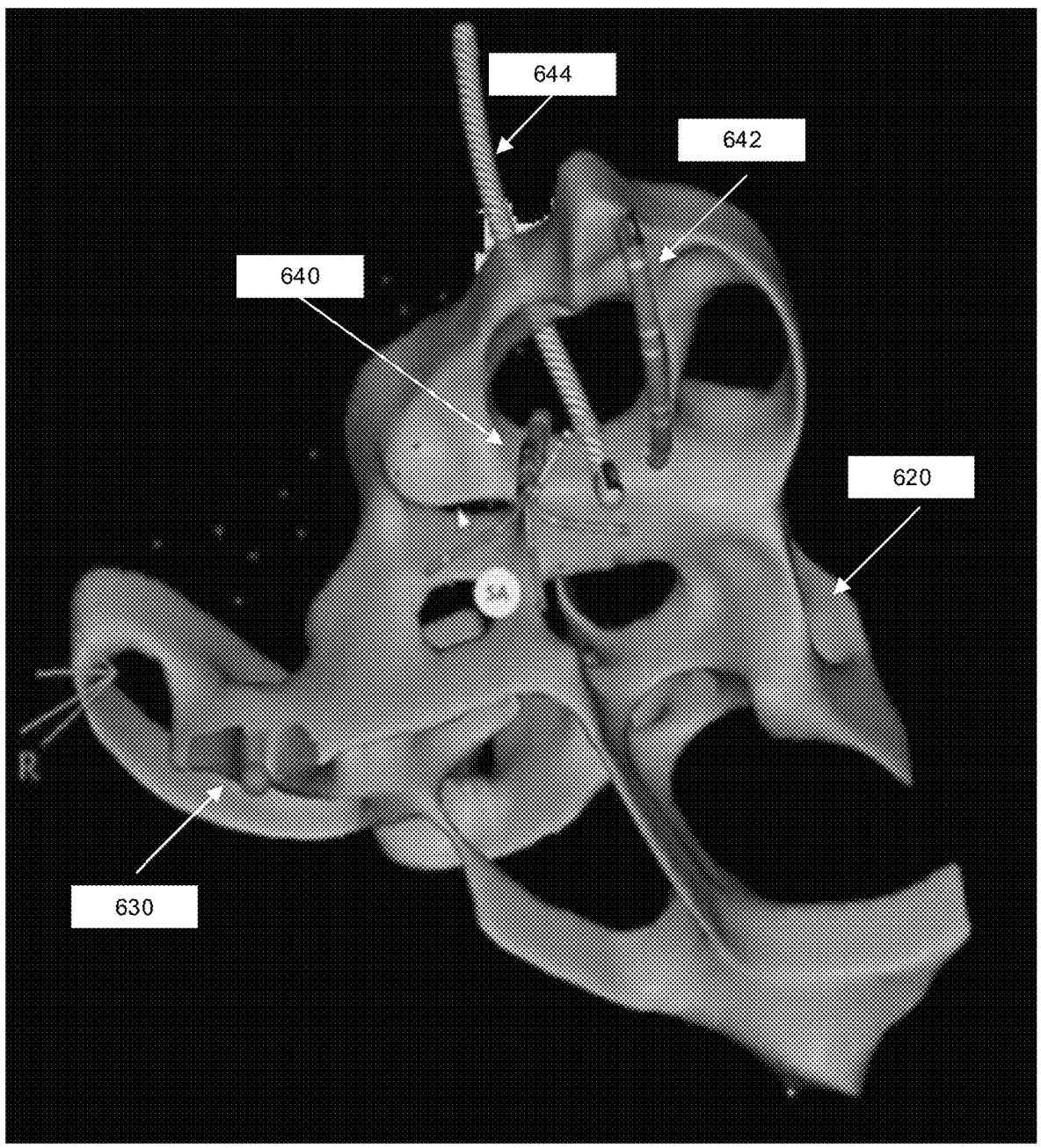
FIG. 6 illustrates an example electro-anatomical map, based on which one or more features of the disclosure may be implemented.

FIG. 6 illustrates an example electro-anatomical map 600, based on which one or more features of the disclosure may be implemented. The electro-anatomical map 600 may include a 3D reconstruction of an anatomical section of the heart 620 (i.e., a 3D surface of the anatomical section's endocardial wall) that the electrophysiological procedure may be focusing on. The physician may rotate the anatomical section into a preferred point of view using a graphical user interface (GUI) provided by an input device 240 of the system 100, 200. Also shown are the catheters 640, 642, 644 that are used in the procedure, rendered at their current location in the heart. For example, a multielectrode catheter (e.g., a Pentaray® catheter) 640, a reference catheter 642, and an ablation catheter 644 may be rendered relative to the rendered anatomical section 620 so that the physician can view the location of each catheter and navigate it through the anatomical section 620. Further, to inform the physician's diagnosis, electrical properties derived from the measured electrical signals are overlaid 630 (color coded) onto the anatomical section at tissue locations at which the respective electrical signals were measured.

An anatomical and an electrical mapping may be implemented using various techniques. In an aspect, the acquisition of measurements (acquired by electrodes of a catheter placed at the anatomical section of interest) may facilitate the 3D reconstruction of the anatomical section's endocardial surface. To reconstruct a surface with sufficient spatial resolution, the physician may need to accumulate measurements at a hundred or more locations at the anatomical section. Acquired measurements may include, in addition to the electrical signals, respective locations, that is, the 3D locations at the endocardial surface the electrical signals were measured from. Out of the acquired 3D locations, the surface of the anatomical section may be reconstructed. In an aspect, the acquired 3D locations may be used to refine an initial reconstruction of the anatomical section that was built in a preliminary procedure based on other imaging modalities, such as ultrasound, computed tomography (CT), or magnetic resonance imaging (MRI). Hence, the system 100, 200 may reconstruct a 3D anatomical representation of the patient's heart, rendering (in an increased detail) an anatomical section of interest 620 on the display 127 to be viewed by the physician.

In addition, the system 100, 200, may overlay electrical properties of tissues on the anatomical mapping. The overlaid electrical properties may be derived from the electrical measurements. Thus, each measurement, acquired by an electrode, may be translated by the system to an electrical property, the value of which may be overlaid at the corresponding location on the rendered surface of the endocardial wall. For example, an electrical property such as a LAT may be overlaid on the endocardial surface, resulting in a LAT map 630. A LAT, derived from a measurement, may represent a difference in time between a reference time and the time at which the measurement's pulse was picked up, for example. In another example, an electrical property such as a voltage may be overlaid on the endocardial surface, resulting in a voltage map. A voltage, derived from a measurement, may represent the voltage amplitude at the time the measurement's pulse was picked up, for example. In an aspect, as more and more measurements are acquired by the physician, the anatomy may be progressively reconstructed and an electrical map may be overlaid upon the reconstructed anatomy in increasing detail (or resolution).

Figure 7:
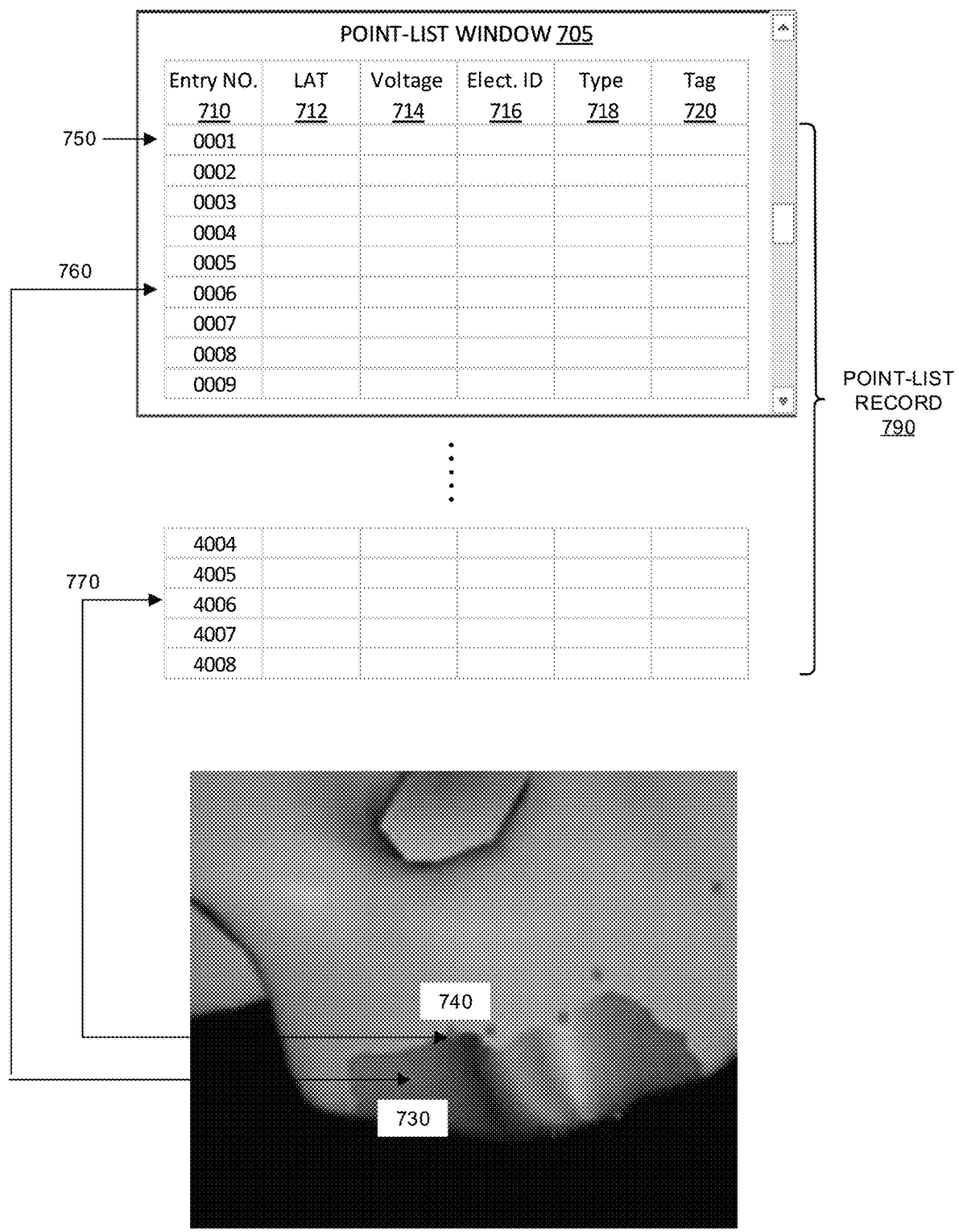
FIG. 7 illustrates an example point-list, based on which one or more features of the disclosure may be implemented.

Along with the electro-anatomical map 600, the system 100, 200 may present data associated with measurements acquired by the physician in a list, namely a point-list (described in reference to FIG. 7). Both the electro-anatomical map and the corresponding point-list may be instrumental for determining a therapeutic course of action, for example, for performing tissue ablation that may alter the propagation of the heart's electrical activity and restore normal heart rhythm.

FIG. 7 illustrates an example point-list 700, based on which one or more features of the disclosure may be implemented. Each entry (i.e., each row 750) of the point-list 700 may contain data elements that correspond to a measurement acquired by an electrode of a catheter employable by the system 100, 200. As a physician in an electrophysiological procedure places a catheter (e.g., one of the catheters described in reference to FIGS. 4-6) at a location in the endocardial surface to acquire electrical signals, the system 100, 200 may record the measured signals and associated data in respective entries of the point-list. The physician may then be presented with a segment of the point-list record 790 in a scrollable window 705. Each entry in the point-list is associated with an electrode's location and the electrode's measured electrical signal, and may contain data elements 710-720. For example, a data element may be an electrical property such as a LAT 712 or a voltage 714 (based on which a LAT map or a voltage map may be generated as described in reference to FIG. 6). Each entry may contain other data elements, such as the entry number 710, identification of the electrode 716 that acquired the measurement associated with the entry, a type 718 that characterizes the measurement, and/or a tag 720 with which the physician may mark the measurement.

The point-list 700 is an instrumental tool aiding the physician's analysis of regions of abnormal electrical activity. Typically, the physician examines the point-list during a procedure to identify abnormality, comparing entries' data (such as the LAT or the voltage data elements). For example, the physician may examine data across entries to identify and eliminate outliers that may be caused by electrodes that were not in sufficient contact with the tissue. However, the physician's survey and analysis of data from the point-list may be complicated by the fact that the list entries that correspond to locations at the anatomy that are proximate to each other may be positioned far from each other in the list. Since during a procedure a point-list may become large (e.g., including thousands of entries), entries that contain data that correspond to tissue locations within an anatomical neighborhood of interest may be thousands of entries a part. Thus, examining these entries against each other in the point-list window 705 may be impractical. For example, measurements acquired from tissue locations 730 and 740 (that are spatially close to each other) may be associated with entry number 0006 760 and entry number 4006 770 that, as illustrated, 4000 entries apart from each other. To address this shortcoming, aspects disclosed herein link the point-list to the anatomy as disclosed in detail below.

Figure 8:
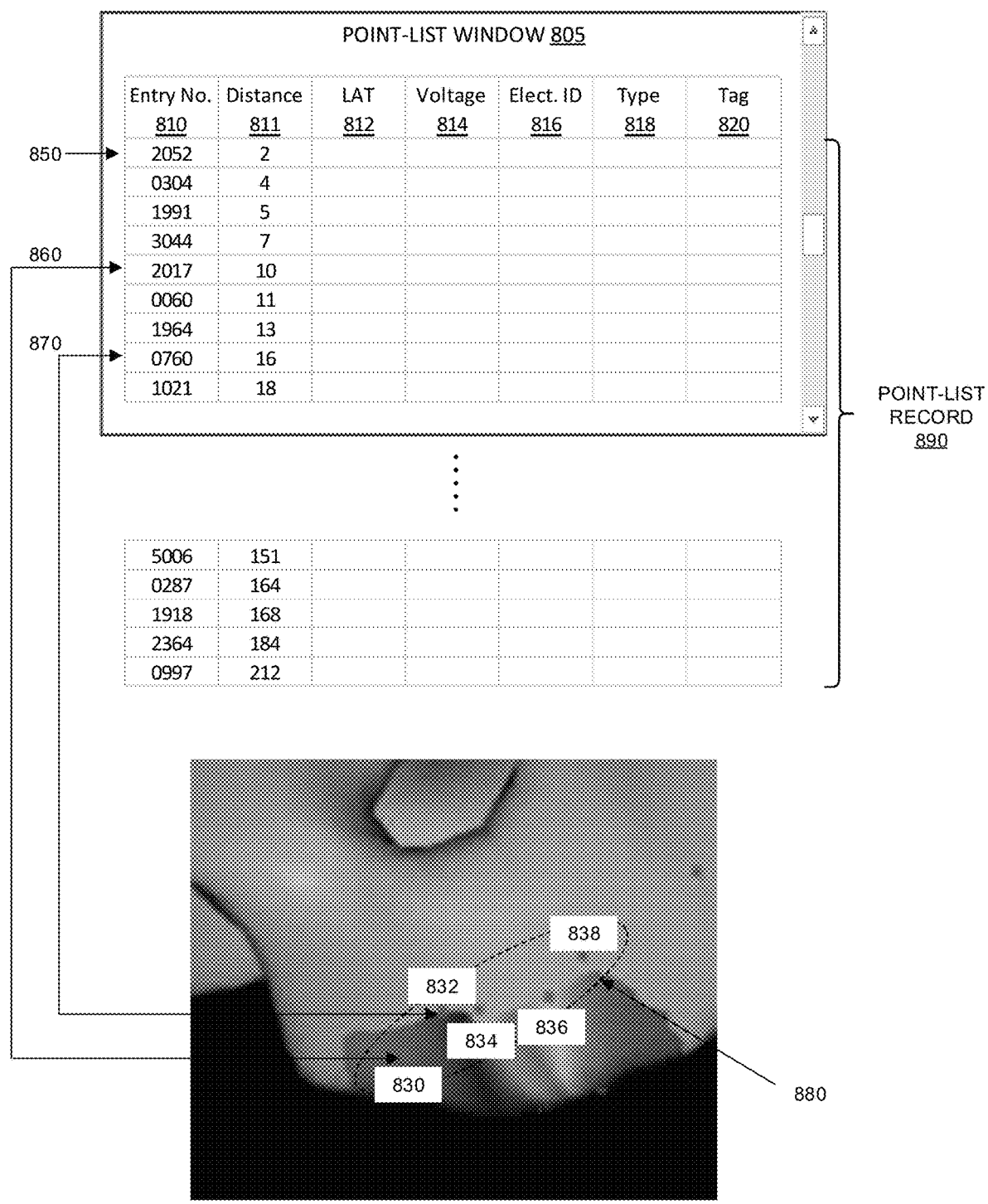
FIG. 8 illustrates an example anatomy-linked point-list, based on which one or more features of the disclosure may be implemented.

FIG. 8 illustrates an example anatomy-linked point-list 800, based on which one or more features of the disclosure may be implemented. Each entry (i.e., each row 850) of the point-list 800 may contain data elements that correspond to a measurement acquired by an electrode of a catheter employable by the system 100, 200. As a physician in an electrophysiological procedure places a catheter at a location in the endocardial surface to acquire electrical signals, the system 100, 200 may record the measured signals and associated data in respective entries of the point-list. The physician may then be presented with a segment of the point-list record 890 in a scrollable window 805. As mentioned before, each entry in the point-list is associated with an electrode's location and the electrode's measured electrical signal, and may contain data elements 810-820. For example, a data element may be an electrical property such as a LAT 812 or a voltage 814. Each entry may contain other data elements, such as the entry number 810, identification of the electrode 816 that acquired the measurement associated with the entry, a type 818 that characterizes the measurement, and/or a tag 820 with which the physician may mark the measurement. Further, each entry may contain a data element of distance 811 that may be used to link the point-list to an anatomical region of interest, according to aspects disclosed herein.

The data entries in a point-list 800 may be linked to an anatomical region of interest defined by one or more anchor points 830-838. The anchor points 830-838 may be manually selected by the physician or automatically determined by the system 100, 200, as described below. Thus, the anchor points may define a neighborhood on the surface of the anatomy—i.e., the anatomical region of interest 880—that the physician wishes to focus the analysis on. The system 100, 200, may then compute for each entry from the point-list 800 a distance between the location associated with the entry (that is, the electrode's location at which the measurement associated with the entry was acquired) and the anchor points. For example, the computed distance may be a minimum distance out of geodesic distances, where each geodesic distance is defined as the distance measured along the anatomical surface from the electrode's location to one of the anchor points. Once a distance 811 is computed for each entry in the point-list, the point-list may be manipulated with respect to an anatomical region of interest defined by the anchor points 830-838. That is, the point-list 800 may be navigated, filtered, or visualized based on the distances 811 of respective entries, as further explained below.

In an aspect, the physician may manually select one or more anchor points by, for example, use of GUI provided by the input device 240 of the system 100, 200. For example, the physician may click on the rendered anatomy to select image points relative a region of interest 880 and the system 100, 200 may translate the selected image points to the corresponding 3D points (on the reconstructed anatomical surface) that constitute the anchor points, e.g., 830-838. Alternatively, the physician may click on one image point, for example, at the center of the region of interest 880, and the system 100, 200 may be set to select anchor points (on the reconstructed anatomical surface) within a predetermined neighborhood of the selected point. In another aspect, the one or more anchor points may be determined based on the current position of a catheter. For example, as the physician advances a multielectrode catheter along the endocardial wall, the current location of each electrode of the catheter (as established by the system 100, 200) may be used as an anchor point. Alternatively, the system 100, 200 may be set to select anchor points (located on the constructed anatomical surface) within a predetermined neighborhood of the current position of the catheter's distal end, for example.

According to aspects disclosed herein, once the point-list 800 generated by the system 100, 200 is linked to an anatomical region of interest, various operations may be performed to improve the physician's navigation through the point-list record 890. A physician that is interested in investigating electrical properties of cardiac tissue within a certain region in the heart may use the system 100, 200 to determine that region as the region of interest by means of anchor points. Following a selection of anchor points, as described above, each entry in the point-list 800 may have associated with it a distance that is computed relative to the anchor points. The computed distances 811 may be added to the data elements of respective entries in the point-list 800 and may be updated each time the region of interest is changed by the physician—that is, each time a new group of anchor points are determined. Thus, a physician that wishes to investigate a region of interest 880 (e.g., defined by the anchor points 830-838) may sort the point-list record 890 based on the distance data elements 811 so that entries of the list having a smaller distance will appear before those having a larger distance. Sorted by distance, data entries associated with measurements acquired from locations in close proximity (relative to the region of interest) appear close to each other in the point-list. For example, measurements acquired from tissue locations 830 and 832 (that are spatially close to each other) are associated with entry number 2017 860 and entry number 0760 870 that, as illustrated, are only 3 entries apart from each other. Thus, data entries associated with measurements acquired from cardiac tissue in close proximity can now be visually inspected in the point-list window 805 and can be easily compared to each other by the physician.

When the point-list record 890 is sorted based on distance 811, data entries with a distance 811 that is below a predetermined threshold may be grouped together and may be viewed together in the point-list window 805 (namely, a primary window). In an aspect, data entries with a distance 811 that is below a predetermined threshold may be viewed in a secondary window (not shown). In that aspect, the primary window 805 may be used to display the remainder of the points or all the points in the record 890. Viewing the point-list in two windows may be useful, for example, if each window provides a different view of the point-list record 890. For example, each window may present a different subset of the entries derived based on different filters, as described below.

In an aspect, each point-list window (e.g., a primary 805 or a secondary window) may have different filters associated with it. Accordingly, entries in the point-list 800 may be filtered based on various criteria. The point-list may be filtered with respect to any of its data element 810-820. For example, entries with LAT 812 above a predetermined threshold may be filtered out of the list. Furthermore, filtering may be performed based on a function of several data elements (e.g., a Boolean function). For example, entries with LAT 812 above a predetermined threshold and distance 811 above another predetermined threshold may be filtered out of the list, resulting in a more manageable and relevant list. A filtering function may be determined by the physician or may be determined automatically by the system 100, 200, e.g., based on criteria determined by the physician. For example, a criterion for filtering may be if a certain data element is above x times of the data element's standard deviation.

Navigation through the point-list may be further improved. In an aspect, an entry of the point-list may be selected, dividing the window 805 to a top segment and a bottom segment, so that only entries in the bottom segment of the window may be affected when scrolling down the list. Thus, entries in the top segment of the window, namely pinned entries, are statically shown. The physician, when scrolling down entries shown in the bottom segment of the window, may be able to select (to pin) therefrom other entries of interest. Such pinned entries may then be moved to the top segment of the window and may be compared against other pinned entries in that segment. In an aspect, pointers to entries of the point-list that were accessed may be cached by the system 100, 200 to allow a quick retrieval of last accessed entries. For example, entries that were last edited may be retrieved using the caching mechanism. In another aspect, the history of selected entries, selected through the sorting operation or the filtering operation, described above, may be recorded by the system 100, 200. Thus, the physician may be able to move forward and backward through the recorded history of selected entries. In yet another aspect, the system 100, 200 may allow the physician to indicate entries in the point-list 800 as favorite entries and to perform operations relative to those entries.

The anatomy-link point-list 800, disclosed herein, may also facilitate enhancement of the electro-anatomical map 600. Data associated with the entries or a subset of the entries (e.g., extracted from the point-list record 890 by the application of a sorting or a filtering operation) may be visualized relative to (or overlaid on) the electro-anatomical map 600. For example, the color, transparency, or texture of the rendered anatomy 620 may be altered at the entries' associated locations on the anatomy, possibly, as a function of the respective entries' data elements (e.g., distances 811). In another example, graphical elements may be overlaid on the rendered anatomy 620 at the entries' associated locations on the anatomy, possibly, the graphical elements representative of respective entries' data elements (e.g., distances 811).

Figure 9:
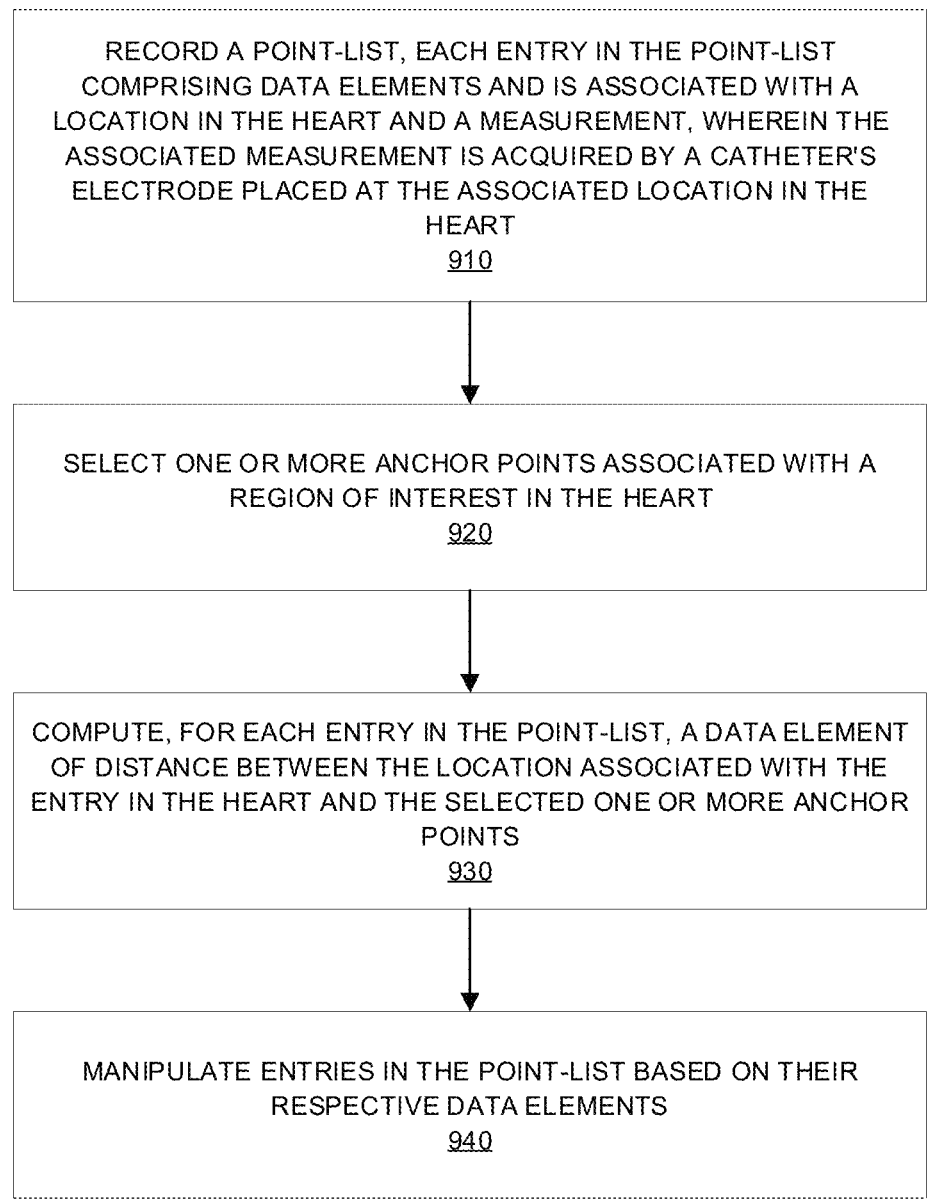
FIG. 9 is a flowchart of an example method for linking a point-list to a 3D anatomy, based on which one or more features of the disclosure may be implemented.

FIG. 9 is a flowchart for an example method 900 for linking a point-list to a 3D anatomy, based on which one or more features of the disclosure may be implemented.

The method 900 begins in step 910 with the recording of a point-list 800. As described in reference to FIG. 8, each entry in the point-list 800 may contain data elements and may be associated with a location in the heart and a measurement, acquired by a catheter's electrode placed at the associated location in the heart. In step 920, one or more anchor points may be selected, the selected anchor points may be associated with a region of interest in the heart. As described above, the one or more anchor points may be selected manually by the physician or may be determined based on the current location of the catheter. Then, for each entry in the point-list, in step 930, a data element of distance is computed. The computed distance is between the entry's associated location (that is, the location of the entry's associated electrode) in the heart and the selected one or more anchor points. For example, the distance computed may be a minimum distance out of geodesic distances, where each geodesic distance is defined as the distance measured along the anatomical surface from the electrode's location to one of the anchor points. Once a distance data element is computed for each entry in the point-list 800, in step 940, the point-list may be manipulated based on the respective data elements. For example, the point-list may be navigated, filtered, or visualized based on the data elements, including the computed distances 811, as explained above.

Although features and elements are described above in particular combinations, one of ordinary skill in the art will appreciate that each feature or element can be used alone or in any combination with the other features and elements. In addition, although process steps are described above in a particular order, the steps can be performed in other desirable orders.

The methods, processes, modules, and systems described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, read only memory (ROM), random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

Further embodiments herein may be formed by supplementing an embodiment with one or more element from any one or more other embodiments herein, and/or substituting one or more elements from one embodiment with one or more elements from one or more other embodiment herein.

It is understood, therefore, that the disclosed subject matter is not limited to the particular embodiments disclosed, but is intended to cover all modifications which are within the spirit and scope of the disclosure as defined by the appended claims, the above description, and/or shown in the attached drawings.

What is claimed is:

1. A method for improving navigation of data collected from a heart of a patient, the method comprising:
   recording a point-list, wherein each entry in the point-list includes a location in the heart and a measurement acquired by an electrode of a catheter placed at the location in the heart;
   rendering a representation of at least a portion of the heart;
   selecting on the representation one or more anchor points associated with a region of interest in the heart;
   computing, for each entry in the point-list, a distance between the location associated with the entry in the point-list and the selected one or more anchor points;
   manipulating one or more entries in the point-list based on the distance computed; and
   overlaying graphical elements on the representation, wherein the graphical elements are representative of a result of the manipulating.

2. The method of claim 1, wherein the distance for each entry in the point-list is a minimum distance out of geodesic distances, each geodesic distance is computed between an associated location in the heart and one of the selected one or more anchor points.

3. The method of claim 1 wherein
   the representation is a three-dimensional reconstruction of the heart.

4. The method of claim 1, wherein the selected one or more anchor points correspond to respective locations of the electrode of the catheter.

5. The method of claim 1, wherein the selected one or more anchor points are determined relative to a location of a distal end of the catheter.

6. The method of claim 1, wherein each entry in the point-list further comprises comprise electrical properties of tissues that are derived from the measurement of a respective entry.

7. The method of claim 1, wherein the manipulating comprises sorting the one or more entries based on the distance.

8. The method of claim 1, wherein the manipulating comprises filtering out entries from the point-list based on a filtering function.

9. The method of claim 8, wherein the filtering function is determined automatically based on one or more predetermined criteria.

10. The method of claim 1, wherein the manipulating comprises displaying the point-list in multiple windows and the manipulating is performed independently in each window.

11. The method of claim 1, wherein the manipulating comprises displaying the point-list in multiple sections of a window and the manipulating is performed independently in each section of the window.

12. The method of claim 1, further comprising:
    dividing a window displaying the point-list to a top segment and a bottom segment, wherein the one or more entries that are part of the top segment are statically shown and the one or more entries that are part of the bottom segment are scrollable; and
    moving an entry from the bottom segment to the top segment in response to a pinning operation of the entry.

13. The method of claim 1, further comprising caching pointers to the one or more entries in the point-list that are last accessed.

14. The method of claim 1, further comprising recording history of operations, including a sorting operation or a filtering operation of the one or more entries in the point-list.

15. The method of claim 1, further comprising:
    selecting one or more favorite entries of the entries in the point-list, wherein the manipulating comprises manipulating the selected favorite entries.

16. A system for improving navigation of data collected from a heart of a patient, comprising:
    at least one processor; and
    memory storing instructions that, when executed by the at least one processor, cause the system to:
    record a point-list, each entry in the point-list includes a location in the heart and a measurement that is acquired by an electrode of a catheter placed at the location in the heart;
    render a representation of at least a portion of the heart;
    select on the representation one or more anchor points associated with a region of interest in the heart;
    compute, for each entry in the point-list, a distance between the location associated with the entry in the heart and the selected one or more anchor points;
    manipulate one or more entries in the point-list based on the distance computed; and
    overlay graphical elements on the representation, wherein the graphical elements are representative of a result of the manipulating.

17. The system of claim 16, wherein the distance for each entry in the point-list is a minimum distance out of geodesic distances, each geodesic distance is computed between an associated location in the heart and one of the selected one or more anchor points.

18. The system of claim 16, wherein
    the representation is a three-dimensional reconstruction of the heart.

19. The system of claim 16, wherein the selected one or more anchor points correspond to respective locations of the electrode of the catheter.

20. The system of claim 16, wherein the selected one or more anchor points are determined relative to a location of a distal end of the catheter.

21. The system of claim 16, wherein the manipulating comprises sorting the entries based on their respective distance data elements.

22. The system of claim 16, wherein the manipulating comprises filtering out entries from the point-list based on a filtering function.

23. A non-transitory computer-readable medium comprising instructions executable by at least one processor to perform a method for improving navigation of data collected from a heart, the method comprising:

recording a point-list, wherein each entry in the point-list includes a location in the heart and a measurement acquired by an electrode of a catheter placed at the location in the heart;
rendering a representation of at least a portion of the heart;
selecting on the representation one or more anchor points associated with a region of interest in the heart;
computing, for each entry in the point-list, a distance between the location associated with the entry in the point-list and the selected one or more anchor points;
manipulating one or more entries in the point-list based on the distance computed; and
overlaying graphical elements on the representation, wherein the graphical elements are representative of a result of the manipulating.

24. The non-transitory computer-readable medium of claim 23, wherein the distance for each entry in the point-list is a minimum distance out of geodesic distances, each geodesic distance is computed between an associated location in the heart and one of the selected one or more anchor points.

25. The non-transitory computer-readable medium of claim 23 wherein
the representation is a three-dimensional reconstruction of the heart.

26. The non-transitory computer-readable medium of claim 23, wherein the selected one or more anchor points correspond to respective locations of the electrode of the catheter.

27. The non-transitory computer-readable medium of claim 23, wherein the manipulating comprises sorting the entries based on their respective distance data elements.

28. The non-transitory computer-readable medium of claim 23, wherein the manipulating comprises filtering out entries from the point-list based on a filtering function.

* * * * *

UNITED STATES PATENT AND TRADEMARK OFFICE
CERTIFICATE OF CORRECTION

| | |
|---|---|
| PATENT NO. | : 12,156,737 B2 |
| APPLICATION NO. | : 17/502578 |
| DATED | : December 3, 2024 |
| INVENTOR(S) | : Fady Massarwa et al. |

It is certified that error appears in the above-identified patent and that said Letters Patent is hereby corrected as shown below:

In the Specification

In Column 1, Line 19, delete "such the" and insert -- such as the --, therefor.

In Column 5, Line 62, delete "change" and insert -- changed --, therefor.

In Column 9, Line 43, delete "and or" and insert -- and/or --, therefor.

In Column 11, Line 43, delete "a part." and insert -- apart. --, therefor.

In Column 12, Line 36, delete "relative a" and insert -- relative to a --, therefor.

In the Claims

In Column 15, Line 27, in Claim 1, delete "representation" and insert -- representation of --, therefor.

In Column 15, Line 52, in Claim 6, delete "comprises comprise" and insert -- comprises --, therefor.

In Column 16, Line 25, in Claim 16, delete "the a" and insert -- the --, therefor.

In Column 16, Line 34, in Claim 16, delete "representation" and insert -- representation of --, therefor.

In Column 17, Line 6, in Claim 23, delete "representation" and insert -- representation of --, therefor.

Signed and Sealed this
Twenty-first Day of January, 2025

Coke Morgan Stewart
*Acting Director of the United States Patent and Trademark Office*